(12) United States Patent
Nakamura et al.

(10) Patent No.: US 8,887,331 B2
(45) Date of Patent: Nov. 18, 2014

(54) HEAD HOLDER, IMAGING TABLE, AND X-RAY CT APPARATUS

(75) Inventors: Naoki Nakamura, Tokyo (JP); Kiyoshi Matsumura, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 58 days.

(21) Appl. No.: 13/553,567

(22) Filed: Jul. 19, 2012

(65) Prior Publication Data

US 2013/0028391 A1 Jan. 31, 2013

(30) Foreign Application Priority Data

Jul. 28, 2011 (JP) .................. 2011-165179

(51) Int. Cl.
- *A61G 13/12* (2006.01)
- *A61B 6/04* (2006.01)
- *A47C 20/04* (2006.01)

(52) U.S. Cl.
CPC .................. *A61B 6/0428* (2013.01)
USPC ............ 5/634; 5/640; 5/633; 5/657

(58) Field of Classification Search
USPC ............. 5/640, 633, 634, 657
See application file for complete search history.

(56) References Cited

U.S. PATENT DOCUMENTS

| | | | | |
|---|---|---|---|---|
| 224,272 A * | 2/1880 | Beull | | 297/118 |
| 1,151,894 A * | 8/1915 | Meinecke | | 5/634 |
| 3,763,509 A * | 10/1973 | Mittendorf | | 5/640 |
| 4,266,759 A | 5/1981 | Liebman | | |
| 4,853,993 A * | 8/1989 | Walpin et al. | | 5/634 |
| 4,910,819 A | 3/1990 | Brown | | |
| 5,448,790 A * | 9/1995 | Saro et al. | | 5/657 |
| 5,667,275 A | 9/1997 | Takeda | | |
| 6,199,233 B1 | 3/2001 | Kantrowitz et al. | | |
| 6,376,846 B2 | 4/2002 | Livingston | | |
| 6,618,613 B1 | 9/2003 | Shukla et al. | | |
| 6,684,431 B2 * | 2/2004 | Splane, Jr. | | 5/657 |
| 6,735,798 B1 * | 5/2004 | Sekizawa | | 5/632 |
| 7,325,266 B1 * | 2/2008 | Olson et al. | | 5/630 |
| 7,555,794 B2 * | 7/2009 | Zelnik et al. | | 5/632 |
| 7,866,742 B2 | 1/2011 | LaPointe | | |
| 7,909,036 B2 | 3/2011 | Kusner, Jr. et al. | | |
| 2003/0145387 A1 * | 8/2003 | Karafa et al. | | 5/733 |
| 2005/0005358 A1 * | 1/2005 | DuDonis | | 5/632 |
| 2005/0193492 A1 * | 9/2005 | Yoshino | | 5/632 |
| 2009/0144905 A1 * | 6/2009 | Javaruski et al. | | 5/630 |

FOREIGN PATENT DOCUMENTS

| | | |
|---|---|---|
| JP | 07299059 B2 | 11/1995 |
| JP | 09075333 | 3/1997 |
| JP | 2002291731 | 10/2002 |

* cited by examiner

*Primary Examiner* — Robert G Santos
*Assistant Examiner* — Ifeolu Adeboyejo
(74) *Attorney, Agent, or Firm* — Armstrong Teasdale LLP

(57) ABSTRACT

A head holder for imaging is provided. The head holder includes a base, a head rest configured to receive a head of a subject, the head rest pivotally connected to the base and rotatable about a rotational axis defined through a lower end of the head rest, and a stopper configured to be inserted between the base and the head rest to support the head rest and fix the head rest at a tilt angle that corresponds to an insertion position of the stopper in a body axis direction of the subject.

11 Claims, 5 Drawing Sheets

HEAD HOLDER, IMAGING TABLE, AND X-RAY CT APPARATUS

CROSS REFERENCE TO RELATED APPLICATIONS

This application claims the benefit of Japanese Patent Application No. 2011-165179 filed Jul. 28, 2011, which is hereby incorporated by reference in its entirety.

BACKGROUND OF THE INVENTION

The present invention relates to a head holder on which a head of a subject is mounted, as well as an imaging table and an X-ray CT (Computed Tomography) apparatus having such a head holder.

In recent X-ray CT apparatuses, the scanning gantry without a tilt mechanism has been developed. There are principal reasons for it such as to improve rigidity of a frame to cope with a faster rotational speed of the scanning gantry, an angle range in which the scanning gantry can be tilted being restricted due to an increase in the number of rows of X-ray detector elements, and to reduce the manufacturing cost by eliminating the tilt mechanism.

When obtaining an image of a subject's head using a scanning gantry without a tilt mechanism, a slice axis of a tomogram is aligned with an axis of a head portion. Also, it might be necessary to prevent crystalline lenses, which are highly sensitive to radiation, from being too much exposed. In order to do so, there is a case where it is desired to incline the head portion with respect to an imaging table to form a certain angle.

In view of the above, there is proposed a head holder whose tilt angle of a portion on which a head is mounted can be varied (see for example, Japanese Patent No. 4603712, Japanese Unexamined Patent Publication No. 299059/1995, and Japanese Unexamined Patent Publication No. 75333/1997).

A head holder disclosed in Japanese Patent No. 4603712 is configured such that a portion on which a head is mounted is slidable along a curved surface of a base supporting the portion. Therefore, when a subject is laid on an imaging table and a tilt angle of the head holder is adjusted, an operator such as an imaging engineer has to lift and support the head of the subject and to move the head holder, exhibiting poor workability. Further, when the head holder is slid, a position of a recessed portion on which the head is placed varies. Besides, the way the position varies does not coincide with the way the head portion moves. Therefore, when the tilt angle is adjusted, the subject has to adjust the position by moving his or her body.

Also, a head holder disclosed in Japanese Unexamined Patent Publication No. 299059/1995, and Japanese Unexamined Patent Publication No. 75333/1997 is configured such that a portion on which a head is placed can swing or rotate, but its structure is complicated. In particular, a mechanism to fix the portion on which the head is placed is complicated, causing poor workability in adjustment of the tilt angle.

With such circumstances, improvement in workability of adjusting the tilt angle of the head holder is desired.

BRIEF DESCRIPTION OF THE INVENTION

In accordance with a first aspect, a head holder for imaging is provided. The head holder includes a base, a head rest on which a head of a subject is mounted and which is pivotally connected to the base with a lower end portion in an upper and lower direction along an axis of the mounted head being as a rotational axis, and a stopper which is inserted between the base and the head rest to support the head rest and which fixes the head rest at a tilt angle corresponding to an insertion position in a body axis direction of the subject.

In accordance with a second aspect, a head holder of the first aspect is provided, in which the head rest has a concave curved surface near a center of an upper surface on which part of the head is mounted.

In accordance with a third aspect, a head holder of the first or second aspect is provided, in which the head rest has a manipulating part to be gripped by a hand, when operating a rotational motion, at an upper end portion in an upper and lower direction along the axis of the mounted head.

In accordance with a fourth aspect, a head holder of any one of the first to third aspects is provided, in which the stopper has a handle part on the side opposite to an insertion direction.

In accordance with a fifth aspect, a head holder of any one of the first to fourth aspects is provided, in which at least part of a bottom surface of the base has a curved surface whose curvature is substantially the same as that of a curved surface of a top plate of an imaging table on which the subject is mounted.

In accordance with a sixth aspect, a head holder of any one of the first to fifth aspects is provided, in which the rotational axis is parallel to a horizontal direction which is orthogonal to the body axis direction of the subject.

In accordance with a seventh aspect, a head holder of any one of the first to sixth aspects is provided, in which the stopper is detachably attached to the upper end portion in the upper and lower direction along the axis of the head on the head rest.

In accordance with an eighth aspect, a head holder of the seventh aspect is provided, in which the head rest has, in the upper end portion, an opening in which a part of the stopper fits.

In accordance with a ninth aspect, a head holder of the seventh or eighth aspect is provided, in which the stopper has a surface on which arms or hands of the subject can be placed when the stopper is mounted on the head rest.

In accordance with a tenth aspect, a head holder of any one of the first to ninth aspects is provided, in which the base is made of a plastic resin.

In accordance with an eleventh aspect, a head holder of any one of the first to tenth aspects is provided, in which the head rest is made of urethane foam, or urethane foam and a plastic resin.

In accordance with a twelfth aspect, a head holder of any one of the first to eleventh aspects, in which the stopper is made of urethane foam, a plastic resin, or urethane foam and a plastic resin.

In accordance with a thirteenth aspect, an imaging table including a head is provided. The head holder includes a base, a head rest on which a head of the subject is mounted and which is pivotally connected to the base with a lower end portion in an upper and lower direction along an axis of the mounted head being as a rotational axis, and a stopper which is inserted between the base and the head rest to support the head rest and which fixes the head rest at a tilt angle corresponding to an insertion position in a body axis direction of the subject.

In accordance with a fourteenth aspect, an X-ray CT apparatus including a head holder is provided. The head holder includes a base, a head rest on which a head of the subject is mounted and which is pivotally connected to the base with a lower end portion in an upper and lower direction along an axis of the mounted head being as a rotational axis, and a stopper which is inserted between the base and the head rest to support the head rest and which fixes the head rest at a tilt angle corresponding to an insertion position in a body axis direction of the subject.

In this regard, an "upper and lower direction along an axis of the head" means a direction of a straight line linking a side of the top of the head with a side of the body. The direction from the body side to the top-of-the-head side is an upper direction, and the direction from the top-of-the-head side to the body side is a lower direction.

According to the above aspects, the head rest on which the head is mounted is pivotally connected to the base with its lower end portion being as a rotational axis. Therefore, even with the head in the mounted state, the head rest can be supported and rotated by a small force. Moreover, the stopper is inserted between the base and the head rest to support and fix the head rest. Therefore, simply by changing the insertion position, the rotating position of the head rest can be changed, thereby improving the workability in adjustment of the tilt angle of the head rest.

DETAILED DESCRIPTION OF THE INVENTION

Exemplary embodiments are described below. It is, however, not intended to limit the invention to the precise form disclosed.

Figure 1:
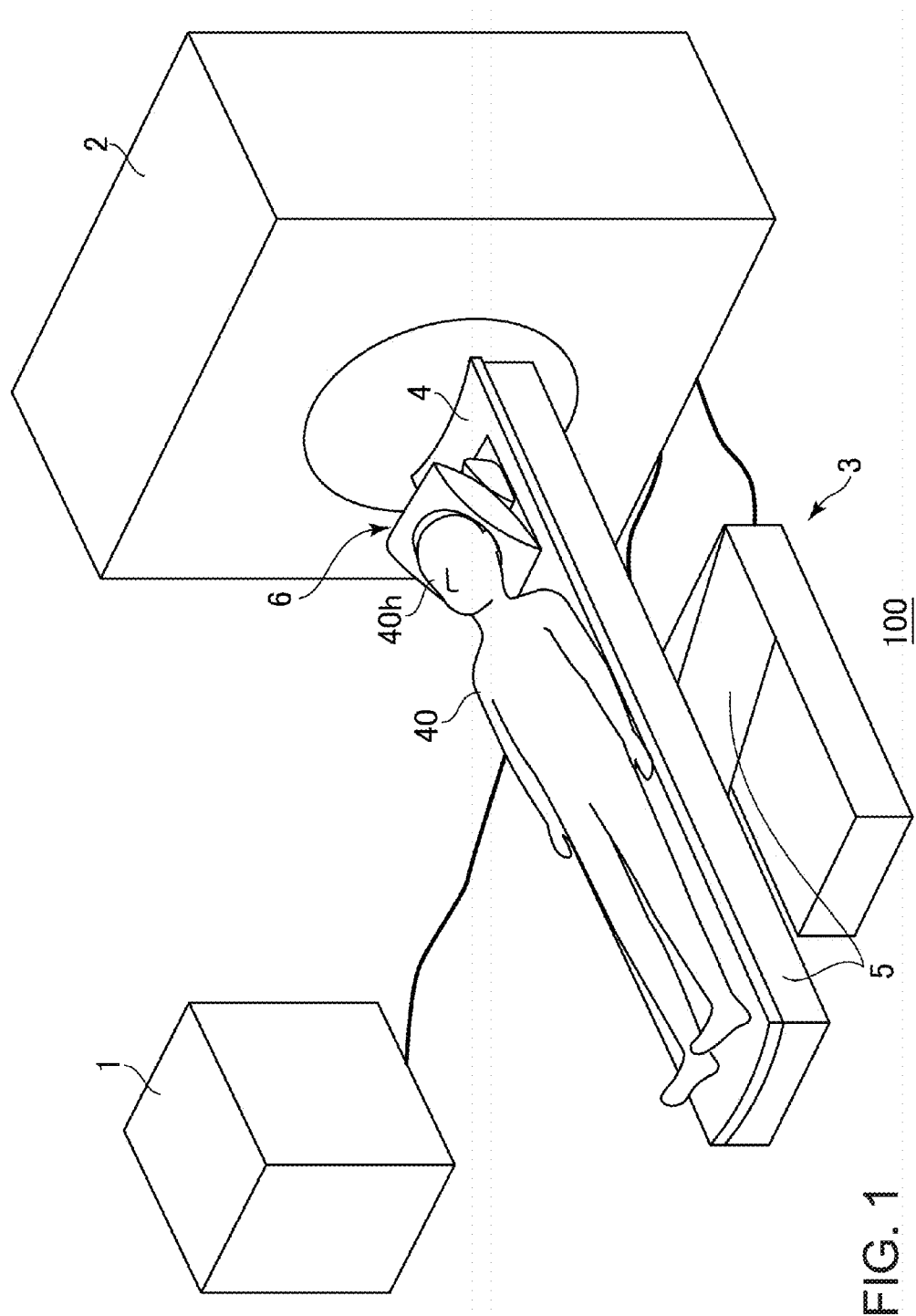
FIG. 1 schematically shows a structure of an exemplary X-ray CT apparatus.

FIG. 1 schematically shows a structure of an exemplary X-ray CT apparatus.

The X-ray CT apparatus 100 includes an operation console 1, a scanning gantry 2, and an imaging table 3.

The operation console 1 controls the scanning gantry 2 and the imaging table 3, and executes an X-ray CT scan. Then, the operation console 1 reconstructs a tomogram based on obtained scan data.

The scanning gantry 2 irradiates a head and a body of a subject 40 laid on the imaging table 3 with X-rays from the periphery thereof. By detecting the X-rays having passed through them, the scanning gantry 2 obtains the scan data.

The imaging table 3 includes a cradle (top plate) 4 on which the subject 40 is laid, a movement controller 5 which moves the cradle 4 in a height direction (y direction) and a horizontal direction (z direction), and puts in and takes out the cradle 4 with respect to a cavity portion which is an imaging space of the scanning gantry 2, and a head holder 6 holding the head of the subject 40 laid on the cradle 4.

Now, a structure of the head holder 6 will be described in detail.

Figure 2:
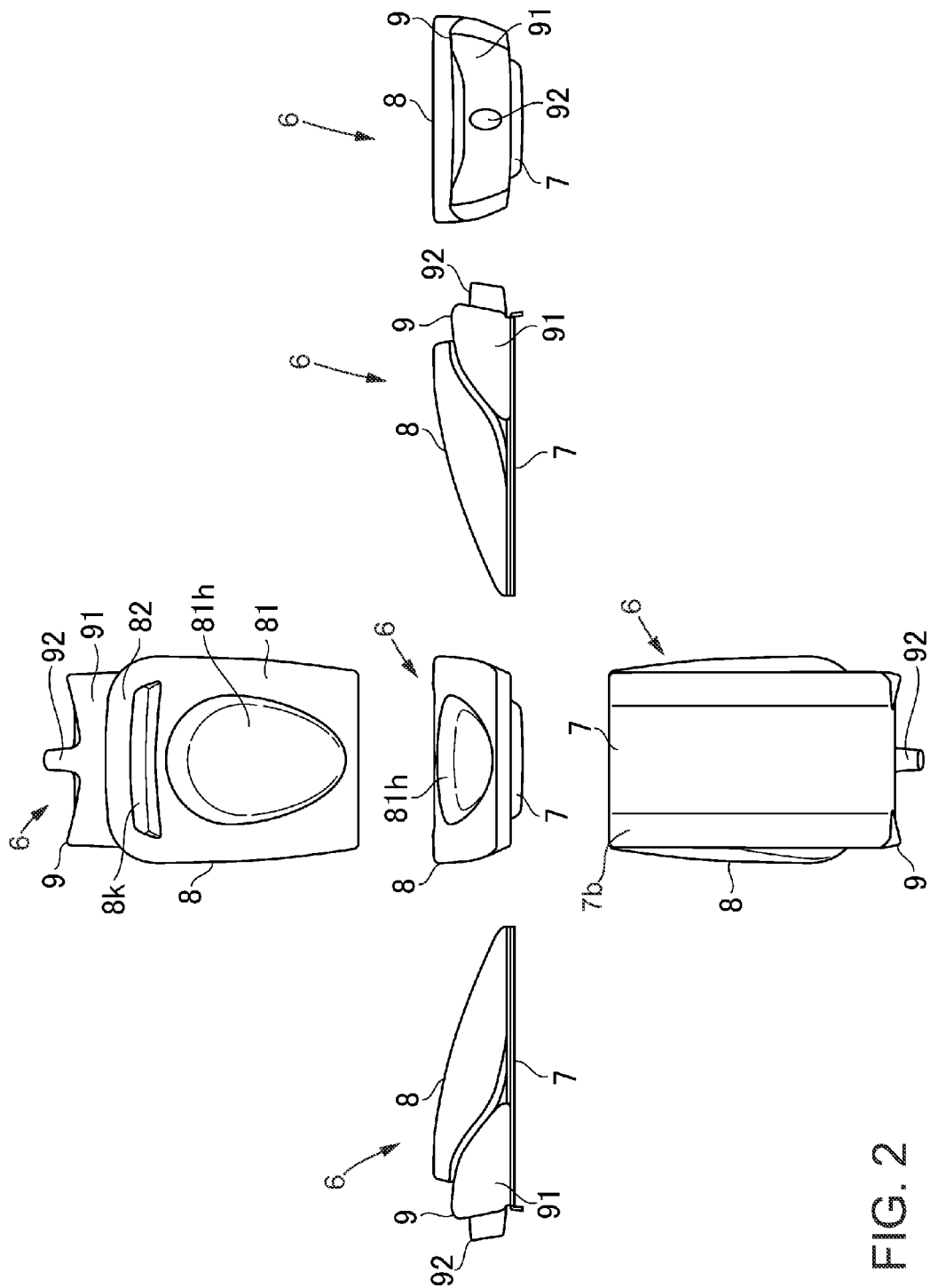
FIG. 2 shows six views of an exemplary head holder.
Figure 3:
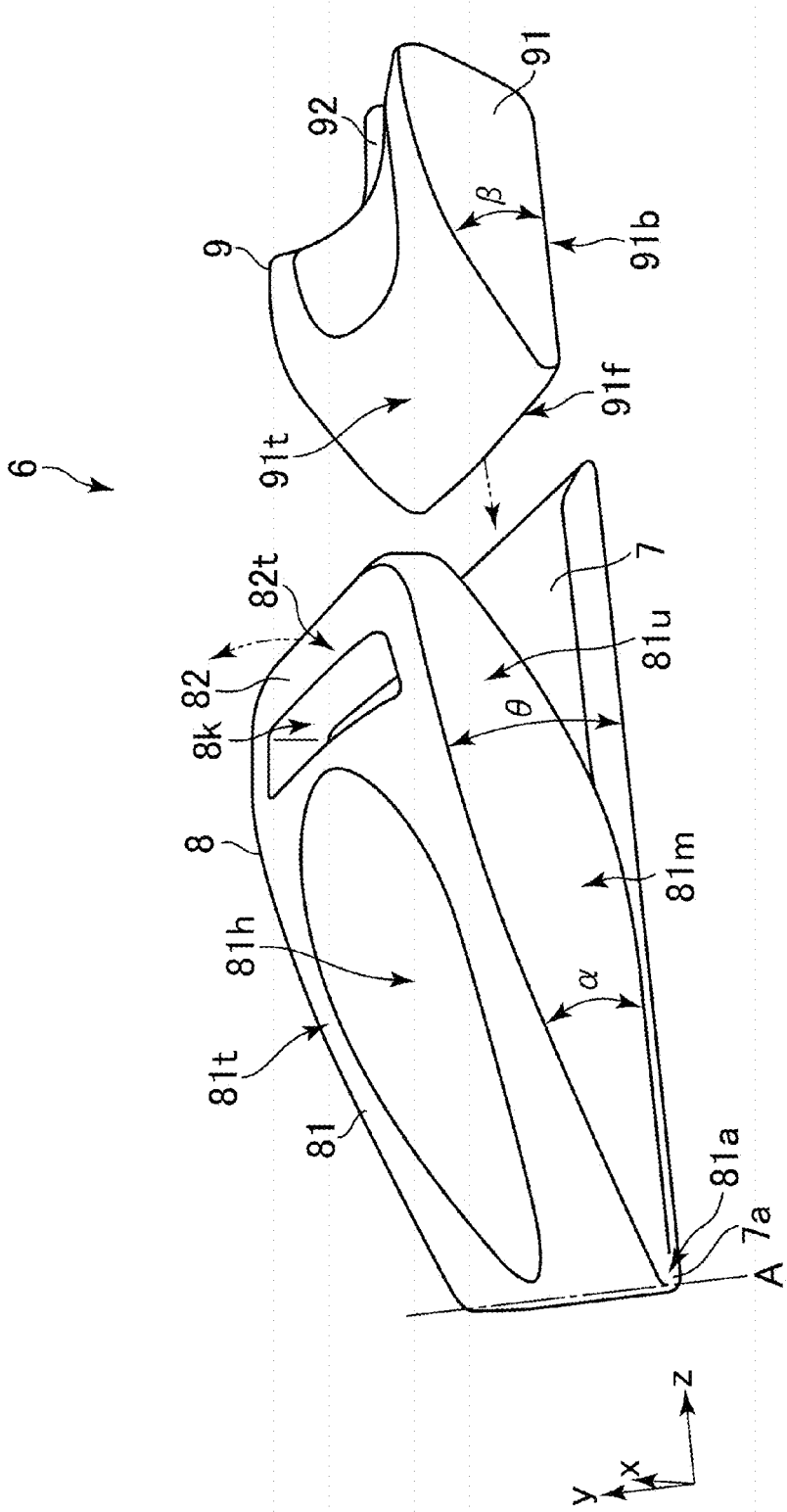
FIG. 3 is a perspective view of the head holder shown in FIG. 2.

FIG. 2 shows six views of the head holder 6, and FIG. 3 is a perspective view of the head holder 6.

As shown in FIGS. 2 and 3, the head holder 6 includes a base 7, a head rest (head mounting part) 8, and a stopper (fixing part) 9.

The base 7 is a portion directly mounted or installed on the cradle 4 on which the subject 40 is laid. The base 7 is generally in the shape of a plate and its plate surface is generally rectangular. The size of the base 7 is, for example, about 250 mm (x direction)×350 mm (z direction)×5 to 10 mm (y direction). The base 7 is made of a material whose X-ray absorption coefficient is small, i.e., plastic resins such as an ABS resin and acrylic. At least part of a bottom surface 7b of the base 7, (e.g., two end portions in the x direction) has a curved surface with substantially the same curvature as that of a curved surface of the cradle 4. Accordingly, the head holder 6 can be mounted on an upper surface of the cradle 4 in a firmly fitted manner.

The head rest 8 is a portion on which a head 40h of the subject 40 is directly mounted, and its tilt angle is adjusted by a rotational motion. The head rest 8 includes a head receiving part 81, and a manipulating part 82, both of which are integrally formed. The overall size of the head rest 8 is, for example, about 250 mm (x direction)×400 mm (z direction)× 150 mm (y direction). A principal portion of the head receiving part 81 of the head rest 8 is made of a low rebounding material whose X-ray absorption coefficient is small, such as urethane foam. The remaining portion is made of a material whose X-ray absorption coefficient is small and rigidity is (e.g., plastic resins such as an ABS resin and acrylic). Further, all of the head rest 8 may be made of urethane foam. Alternatively, only the bottom surface portion may be made of the plastic resin.

The head receiving part 81 is formed such that, in the upper and lower direction of the head 40h to be mounted, a lower end portion 81a is thin and a middle portion 81m or an upper end portion is thick. At around the center of an upper surface 81t of the head receiving part 81, there is formed a concave curved surface 81h on which part of the head 40h, (e.g., a back of the head) is placed. The head receiving part 81 is pivotally connected to the base 7 with a rotational axis A defined through its lower end portion 81a. The rotational axis A is parallel to a horizontal direction (x direction) which is orthogonal to a body axis direction (z direction) of the subject 40. The rotational axis A is realized, for example, when the lower end portion 81a of the head receiving part 81 and one end portion 7a of the base 7 constitute a hinge with use of a nylon cord. When the head receiving part 81 is at a home position, the upper surface 81t of the head receiving part 81 is inclined to a horizontal plane, and its tilt angle α is, for example, about 15° to 35°. Accordingly, with the subject 40 lying on the cradle 4 on the back, the head 40h of the subject 40 can be placed on the head receiving part 81 in a comfortable manner.

The manipulating part 82 is generally in a shape of the letter "U", and is provided at an upper end portion 81u of the head receiving part 81. When the operator turns the head receiving part 81 and changes its tilt angle θ, the manipulating part 82 serves as a grip to be gripped by a hand of the operator. Further, the manipulating part 82 has an upper surface 82t which is relatively gently inclined, and serves as an arm rest on which arms and hands of the subject 40 are placed.

The stopper 9 is inserted between the base 7 and the head rest 8 to support the head rest 8, and fixes the head rest 8 at a tilt angle θ corresponding to an insertion position in the body axis direction (z direction) of the subject 40. The stopper 9 includes a support 91 and a handle part 92, both of which are integrally formed. The overall size of the stopper 9 is, for example, about 200 mm (x direction)×250 mm (z direction)× 100 mm (y direction). The stopper 9 is made of a material whose X-ray absorption coefficient is small, such as urethane foam. In addition, the stopper 9 may also be made of plastic resins such as an ABS resin and acrylic. Alternatively, the stopper 9 may be constituted by combining urethane foam and a plastic resin.

The support 91 is generally in the form of a triangular prism, and its column axis is parallel to the x direction. The angle β made by a bottom surface 91b and an upper surface (slope) 91t of the support 91 is, for example, about 15° to 35°. The support 91 is so inserted as to be sandwiched between the base 7 and the head rest 8 to support the head rest 8. By changing the insertion position of the support 91 in the body axis direction (z direction) of the subject 40, an angle of rotational motion of the head rest 8 is changed and the tilt angle θ can be adjusted.

The handle part 92 is generally in the form of a cylinder, and its column axis is parallel to the z direction. The handle part 92 is provided on the side opposite to the direction in which the stopper 9 is inserted, i.e., on the side of a top of the head 40h of the subject 40. The operator can grip the handle part 92 with his or her hand to insert it between the base 7 and the head rest 8.

According to the head holder 6 of the above structure, by raising the manipulating part 82 of the head rest 8, the head rest 8 is turned about the rotational axis A so that the tilt angle θ of the head rest 8 can be easily varied.

Moreover, with the manipulating part 82 being lifted, by inserting the stopper 9 between the base 7 and the head rest 8, and by adjusting its insertion position, the head rest 8 can be supported and fixed at a desired tilt angle.

Figure 4A:
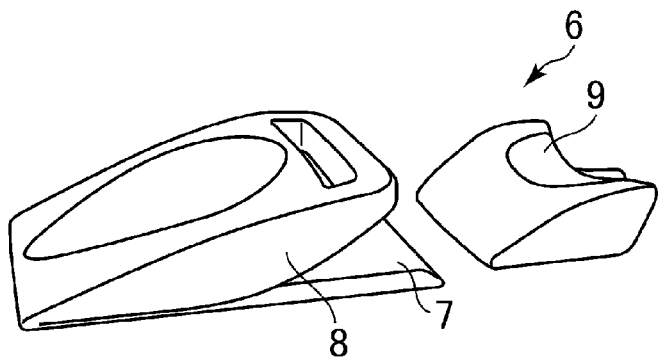
FIGS. 4A-4D are diagrams for explaining a function of adjusting a tilt angle of the head holder shown in FIG. 2.
Figure 4B:
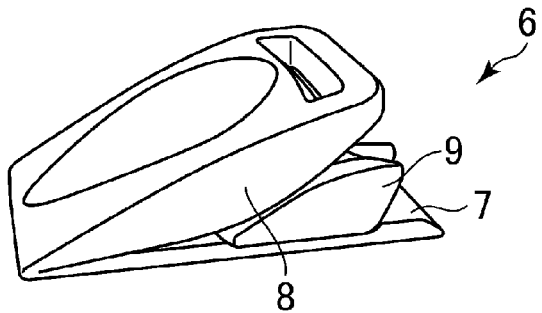
Figure 4C:
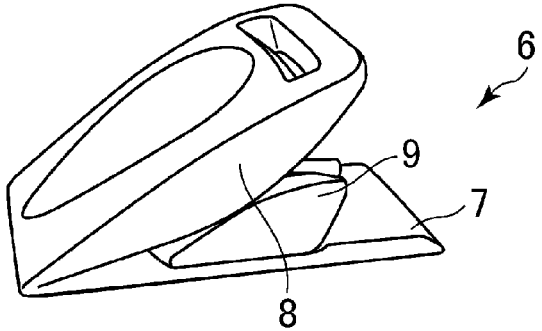
Figure 4D:
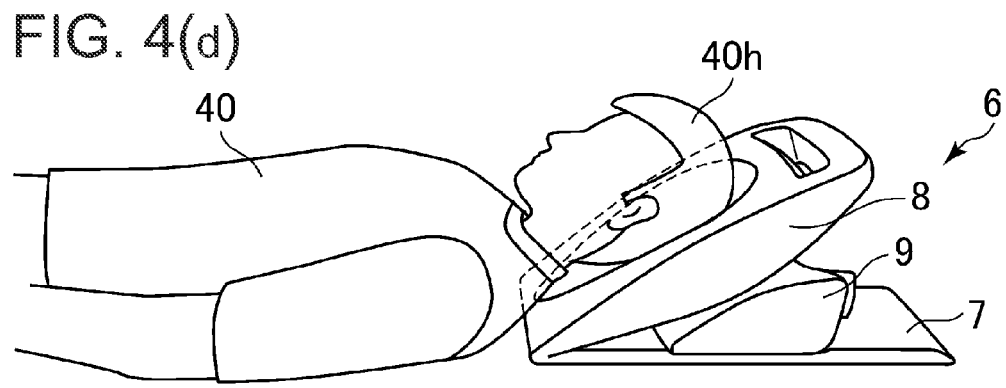

FIGS. 4A-4D are diagrams for explaining a function of adjusting the tilt angle of the head holder. For example, as shown in FIG. 4A, when the stopper 9 is not inserted, the tilt angle θ is smallest. As shown in FIG. 4B, when the stopper 9 is inserted shallowly, the tilt angle θ becomes a little larger and, as shown in FIG. 4C, when the stopper 9 is inserted deeply, the tilt angle θ becomes still larger. As shown in FIG. 4D, the head 40h of the subject 40 is inclined corresponding to the tilt angle θ.

A force required to raise the manipulating part 82 is, according to the principle of lever, smaller than the actual load of the head. If the center of gravity of the head 40h is near the center of the head rest 8, a force required to raise the manipulating part 82 is about half the load concerned. That is, the operator can raise the manipulating part 82 easily with one hand.

Therefore, even in a state where the subject 40 is laid on the cradle 4 and the head 40h is mounted on the head holder 6, the operator can raise the manipulating part 82 with one hand to incline the head rest 8, and insert the stopper 9 with the other hand. Thus, the operator can smoothly set the tilt angle θ of the head rest 8, namely, the tilt angle of the head 40h to a desired angle, achieving good workability.

In addition, the head holder 9 has a very simple structure. Therefore, even when there are spilled on the head holder 9 bodily fluids of the subject, medical liquids such as a contrast medium, vomit, etc., they can be washed away quickly and the liquids do not enter a gap there, exhibiting favorable property for cleaning up.

Moreover, the head holder 9 does not have a mechanical structure. Accordingly, it does not require high rigidity and strength for securing safety. Therefore, it doesn't have to be dependent on a metal material, and an influence thereof on an image quality can also be suppressed.

According to the present embodiment, the head rest 8 and the stopper 9 are structured such that the stopper 9 can be detachably attached to an upper end portion of the head rest 8. As shown in FIG. 3, the head rest 8 has an opening 8k between the head receiving part 81 and the manipulating part 82. The opening 8k is formed as to be fitted in by a tip 91f of the support 91 of the stopper 9. By inserting the stopper 9 into the opening 8k, the stopper 9 can be mounted on the head rest 8. Further, this attaching/detaching method is merely exemplary.

Figure 5A:
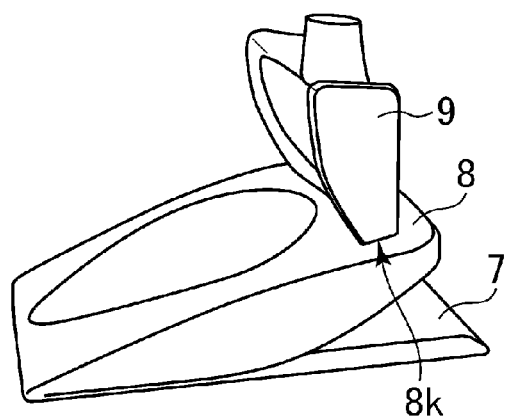
FIGS. 5A and 5B are diagrams for explaining an arm rest function of the head holder shown in FIG. 2.
Figure 5B:
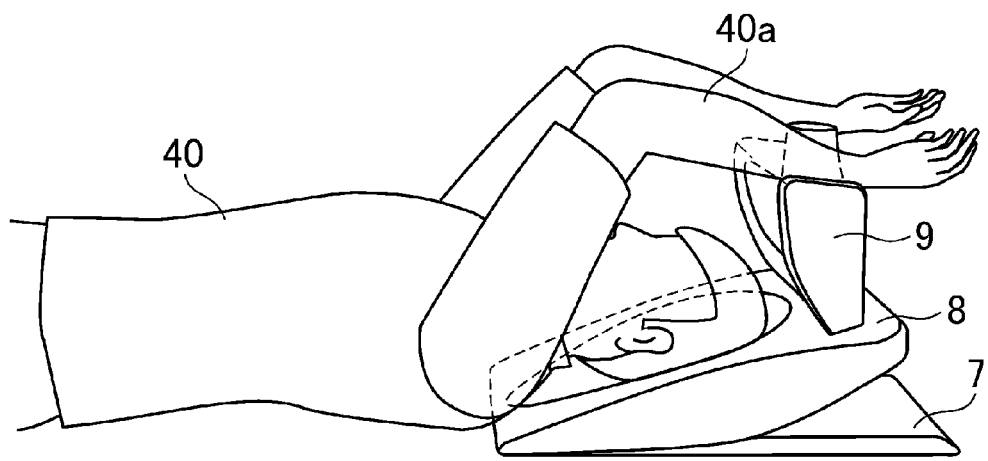

FIGS. 5A and 5B are diagrams for explaining an arm rest function of the head holder. As shown in FIG. 5A, when the stopper 9 is inserted in the opening 8k and mounted, a face on the upper side of the stopper 9, i.e., a face provided on the handle part 92, functions as an arm rest on which arms or hands of the subject 40 can be placed.

In the case of obtaining an image of a portion below the neck of the subject 40, when the arms of the subject 40 enter an imaging region, they may cause an artifact in a tomogram. Therefore, when obtaining the image of the portion below the neck, in order to prevent both the arms from entering the imaging region, generally, the subject 40 is required to put both hands near the top of the head. In this case, both elbows are open right and left. However, when the subject 40 is a person who has difficulty in moving his or her shoulders, or an elderly person, it is painful to take the above posture, causing a burden on the subject 40.

In this embodiment, as shown in FIG. 5B, by using the stopper 9 mounted on the head rest 8 as an arm rest, the subject 40 can put both hands not at the top of the head but at a position closer to the front side. As a result, both the elbows are not opened right and left but can be kept closed, reducing the burden on the subject 40. When obtaining the image of the portion below the neck, it is not necessary to adjust the tilt angle of the head 40h. Therefore, removal of the stopper 9 does not cause a problem.

Moreover, when the stopper 9 is not used or the head holder 6 is stored, if the stopper 9 is mounted on the head rest 8, there will be no problem in securing a place to accommodate the stopper 9. Also, for convenience, it will not be separated from the body portion including the base 7 and the head rest 8.

According to the present embodiment, though not particularly shown, on the upper surface of the base 7 and/or the bottom surface of the stopper 9, there is provided slip-resistance treatment such as coating for increasing a coefficient of friction and attachment of a sheet, which prevents the stopper 9 from shifting due to the load on the head 40h, body movement, mechanical vibration, etc., and further prevents the tilt angle θ of the head rest 8 from varying when obtaining the image.

Also, in the present embodiment, the head rest 8 and the stopper 9 are in the round form not having a plane or an edge in general. As a result, generation of artifacts in a tomogram can be suppressed.

While the invention has been described with reference to exemplary embodiments, the invention is not limited to the embodiments specifically described herein, and many widely different embodiments may be configured without departing from the spirit and the scope of the invention.

The invention claimed is:

1. A head holder for imaging, comprising:
   a base;
   a head rest configured to receive a head of a subject, said head rest pivotally connected to said base and rotatable about a rotational axis defined through a lower end portion of said head rest, wherein said head rest is sized to support substantially just the head of the subject; and
   a stopper configured to be inserted between said base and said head rest to support said head rest and fix said head rest at a tilt angle that corresponds to an insertion position of said stopper in a body axis direction of the subject, wherein said stopper is configured to be detachably attached to an upper end portion of said head rest, said upper end portion including an opening in which a part of said stopper is placed through, and wherein said stopper has a surface on which arms or hands of the subject can be placed when said stopper is mounted on said head rest.

2. A head holder according to claim 1, wherein said head rest has a concave curved surface near a center of an upper surface configured to receive part of the head.

3. A head holder according to claim 1, wherein said head rest has a manipulating part configured to be gripped by a hand when rotating said head rest, said manipulating part located at an upper end portion of said head rest.

4. A head holder according to claim 1, wherein said stopper has a handle part on a side opposite from an insertion direction.

5. A head holder according to claim 1, wherein at least part of a bottom surface of said base has a curved surface whose curvature is substantially the same as that of a curved surface of a top plate of an imaging table configured to support the subject.

6. A head holder according to claim 1, wherein said rotational axis is parallel to a horizontal direction which is orthogonal to the body axis direction of the subject.

7. A head holder according to claim 1, wherein said base is made of a plastic resin.

8. A head holder according to claim 1, wherein said head rest is made of urethane form, or urethane foam and a plastic resin.

9. A head holder according to claim 1, wherein said stopper is made of urethane foam, a plastic resin, or urethane foam and a plastic resin.

10. An imaging table including a head holder, said head holder comprising:
    a base;
    a head rest configured to receive a head of a subject, said head rest pivotally connected to said base and rotatable about a rotational axis defined through a lower end portion of said head rest; and
    a stopper configured to be inserted between said base and said head rest to support said head rest and fix said head rest at a tilt angle that corresponds to an insertion position of said stopper in a body axis direction of the subject, wherein said base has a thickness that enables a user to selectively vary the tilt angle through a continuous range of angles by varying the insertion position of said stopper along said base, wherein said stopper is configured to be detachably attached to an upper end portion of said head rest, said upper end portion including an opening in which a part of said stopper is placed through, and wherein said stopper has a surface on which arms or hands of the subject can be placed when said stopper is mounted on said head rest.

11. An X-ray CT apparatus including a head holder, said head holder comprising:
    a base;
    a head rest configured to receive a head of a subject, said head rest pivotally connected to said base and rotatable about a rotational axis defined through a lower end portion of said head rest; and
    a stopper configured to be inserted between said base and said head rest to support said head rest and fix said head rest at a tilt angle that corresponds to an insertion position of said stopper in a body axis direction of the subject, wherein said base has a thickness that enables a user to selectively vary the tilt angle through a continuous range of angles by varying the insertion position of said stopper along said base, wherein said stopper is configured to be detachably attached to an upper end portion of said head rest, said upper end portion including an opening in which a part of said stopper is placed through, and wherein said stopper has a surface on which arms or hands of the subject can be placed when said stopper is mounted on said head rest.

* * * * *